United States Patent [19]

Carey et al.

[11] Patent Number: 5,674,965
[45] Date of Patent: Oct. 7, 1997

[54] EPOXY COMPOUNDS FOR USE AS COMPONENTS OF AQUEOUS COATING COMPOSITIONS

[75] Inventors: John Gerard Carey, Warrington; John Christopher Padget, Frodsham; David Alan Pears, Chester, all of United Kingdom

[73] Assignee: Zeneca Limited, London, England

[21] Appl. No.: 440,361

[22] Filed: May 12, 1995

[30] Foreign Application Priority Data

May 12, 1994 [GB] United Kingdom ............... 9409525

[51] Int. Cl.$^6$ ..................... C07D 303/16; C07F 7/18; C07F 7/10
[52] U.S. Cl. ................. 528/27; 528/38; 528/403; 528/422; 549/215; 549/547; 549/551
[58] Field of Search ............... 549/215, 547, 549/551; 528/27, 38, 403, 422

[56] References Cited

U.S. PATENT DOCUMENTS

| | | | |
|---|---|---|---|
| 3,682,975 | 8/1972 | Tesoro | 260/348 SC |
| 3,927,024 | 12/1975 | Golitz et al. | 549/215 |
| 4,742,169 | 5/1988 | Paul et al. | 544/388 |
| 5,075,459 | 12/1991 | Kabeta et al. | 549/215 |

FOREIGN PATENT DOCUMENTS

| | | | |
|---|---|---|---|
| 0 281 354 | 9/1988 | European Pat. Off. | C09D 5/02 |
| 0 442 583 A1 | 8/1991 | European Pat. Off. | C09D 163/00 |
| 0 456 347 A1 | 11/1991 | European Pat. Off. | C10M 133/08 |
| 0 522 902 A3 | 1/1993 | European Pat. Off. | C08G 59/12 |

OTHER PUBLICATIONS

Chemical Abstracts: CA 116(5):41762g; CA 118(12):103840h; CA 114(6):44226e; CA 113(24):213293m; CA 93:79310; CA 103(12)88782k; CA 77(22): 140969; CA 72(18):91448c; CA 71(16):71740t.

*Primary Examiner*—D. R. Wilson
*Attorney, Agent, or Firm*—Cushman Darby & Cushman IP Group Pillsbury Madison & Sutro LLP

[57] ABSTRACT

A compound of Formula (1):

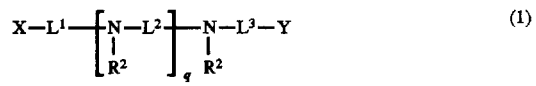

wherein:

X is E—(L$^4$O)$_m$—CO—(T)$_p$;

Y is —Si(R$^1$)$_3$ or X as defined above;

T is O, CH$_2$ or NR$^2$;

P is 0 or 1;

q is 0, 1, 2, 3 or 4;

E comprises an alicyclic or aliphatic epoxy group;

each L$^1$, L$^2$, L$^3$ and L$^4$ independently is an unsubstituted or substituted alkylene group of 1 to 6 carbon atoms wherein any substitution is selected from methyl, amino, ester, hydroxy and ester groups;

m is 0 or 1;

each R$^1$ when Y is —Si(R$^1$)$_3$ is independently unsubstituted alkyl or substituted alkoxy provided that at least one R$^1$ is unsubstituted alkoxy; and each R$^2$ independently is H, —L$^1$X unsubstituted or substituted alkyl wherein any substitution is selected from poly(oxyalkylene), epoxy and hydrolyzable silyl groups, or —CONH(C$_{1-20}$-alkyl). The compounds are useful in coating compositions and films and coatings formed therefrom.

6 Claims, No Drawings

EPOXY COMPOUNDS FOR USE AS COMPONENTS OF AQUEOUS COATING COMPOSITIONS

The present invention relates to epoxy compounds, to aqueous cross-linkable coating compositions containing a specified epoxy compound and a hydroxy and/or carboxy functional polymer, and to films and coatings obtained therefrom.

Industrial coatings are prepared to protect and decorate underlying materials. Originally, these coatings were primarily organic solvent-borne systems, but the development of water-borne coatings has become of increasing interest for a number of reasons. The main reasons for the shift from organic solvent-borne coatings to aqueous alternatives is to decrease the amount of organic solvent emitted into the atmosphere.

In the development of water-borne coatings it has become apparent that the quality of the coating performance is often inferior to that of solvent-borne coatings. It is known that to improve the properties of the aqueous coating the components of the composition need to be designed such that they react and cross-link with the binder on the substrate. Because of the temperature sensitive nature of many of the substrates it is preferred that such compositions will undergo effective cross-linking at ambient temperatures without the need for catalysts, particularly toxic catalysts. We have now devised a highly effective water-based cross-linkable coating composition which can give films and coatings having good mechanical and physical properties.

According to the present invention there is provided a composition comprising water and the following components:

(a) an epoxy compound comprising at least one epoxy group and at least one nitrogen atom; and
(b) a carboxy functional polymer, a hydroxy functional polymer, a polymer having carboxy and hydroxy functionality, or a mixture comprising two or more of said polymers;

provided that when the epoxy compound has only one epoxy group it has at least one hydrolysable silyl group.

The epoxy compound preferably has from 1 to 10, more preferably from 1 to 6, epoxy groups. The epoxy groups are alicyclic or preferably aliphatic. In alicyclic epoxy groups the carbon atoms of the epoxy ring form an alicyclic ring, preferably 5-, 6- or 7-membered (for example a cyclopentane or cyclohexane ring), whereas in aliphatic epoxy groups the carbon atoms of the epoxy ring form an aliphatic chain. Examples of aliphatic epoxy groups are shown in (I) and (II) and alicyclic epoxy groups are shown in (III) and (IV).

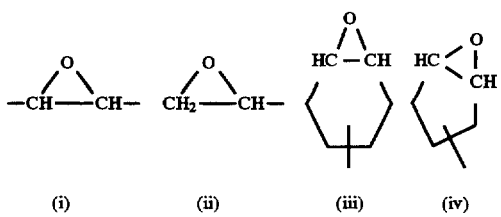

(i)    (ii)    (iii)    (iv)

Examples of epoxy compounds include those having one epoxy group, at least one nitrogen atom and at least one hydrolysable silyl group and those having more than one epoxy group, at least one nitrogen atom and, optionally, one or more hydrolysable silyl groups.

We have found that when the epoxy group in component (a) has an ester group (i.e. —O—C(=O)—) on an adjacent carbon atom then component (a) is a more effective cross-linker for component (b) in terms of the speed and extent of cross-linking. This improvement is particularly marked when the epoxy group is an aliphatic epoxy group.

Examples of epoxy groups having an ester group on an adjacent carbon atom are shown in formulae (V), (VI), (VII) and (VIII) below:

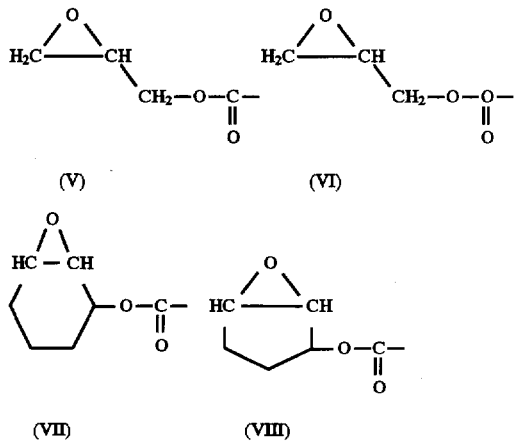

(V)    (VI)

(VII)    (VIII)

Preferably the nitrogen atom in component (a) is a basic nitrogen atom because this leads to particularly effective cross-linking of component (b). The nitrogen atom in component (a) is preferably a secondary amino group, more preferably a tertiary amino group because the epoxy compounds having tertiary amino groups are generally more storage stable. When the nitrogen atom is a secondary amino group it is preferred that the epoxy group(s) is or are 5-, 6- or 7-membered alicyclic rings because these tend to be more storage stable than compounds wherein the epoxy group is aliphatic. The pKa of the basic nitrogen atom preferably lies in the range 1 to 12, more preferably 5 to 11.

It is preferred that component (a) has at least 1 or 2 hydrolysable silyl groups. A hydrolysable silyl group is a group which is convertible to a hydroxysilyl group on treatment with aqueous acid or base. A preferred hydrolysable silyl group is of the formula —Si(R$^1$)$_3$ wherein each R$^1$ independently is optionally substituted alkyl (especially C$_{1-4}$-alkyl) or optionally substituted alkoxy (especially C$_{1-4}$-alkoxy or a poly(oxyalkylene), provided at least one R$^1$ is optionally substituted alkoxy. Preferably all three groups represented by R$^1$ are C$_{1-4}$-alkoxy. When one, two or three of the R$^1$ groups are optionally substituted alkoxy grounds the hydroxysilyl groups obtainable from the hydrolysable silyl group are respectively of formula —SiOH, —Si(OH)$_2$ and —Si (OH)$_3$ wherein the remaining valencies of Si are taken up by the other R$^1$ groups. Examples of hydrolysable silyl groups include each of —Si(OCH$_3$)$_3$, —Si(OCH$_3$)$_2$CH$_3$, —Si(OCH$_2$CH$_3$)$_3$ and —Si(OCH$_2$CH$_3$)$_1$[O(CH$_2$CH$_2$O)$_2$CH$_3$]$_2$.

Component (a) is preferably water-soluble or, more preferably, water-dispersible. Water-solubility and water dispersibility may be achieved by the presence of sulpho, carboxy or poly (oxyalkylene) groups (especially poly (oxyethylene) and poly (oxypropylene) groups). The poly(oxyalkylene) groups may be attached to the nitrogen atom in component (a) or, if present, to the silicon atom in the hydrolysable silyl group.

A preferred epoxy compound which may be used as component (a) is of the Formula (1):

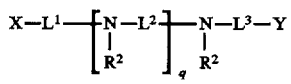 (1)

wherein:

X is E—(L⁴—O)$_m$—(CO)$_n$—(T)$_p$—;
Y is —Si(R¹)$_3$ or X as hereinbefore defined;
T is O, CH$_2$ or NR²;
P is 0 or 1;
q is 0, 1, 2, 3 or 4;
E comprises an alicyclic or aliphatic epoxy group;
each L¹, L², L³ and L⁴ independently is a an unsubstituted or substituted alkylene group of 1 to 6 carbon atoms where any substitution is with at least one group selected from methyl, amino, ether, hydroxy and ester groups;
m and n are each independently 0 or 1;
each R¹ when Y is —Si(R¹)$_3$ is independently unsubstituted alkyl or unsubstituted alkoxy provided that at least one R¹ is unsubstituted alkoxy; and
each R² independently is H—L¹X, unsubstituted or substituted alkyl wherein any substitution is with at least one group selected from poly(oxyalkylene), epoxy and hydrolyzable silyl groups, or CONH(C$_{1-20}$-alkyl).

When q is 2, 3 or 4 each L² may be the same or different.

Compounds of Formula (1) wherein n is 1 form a further feature of the invention preferably m and n are both 1. Preferably p is 0.

In a preferred epoxy compound of Formula (1), m=n=q=1; p=0; L¹, L², L³ and L⁴ are unsubstituted alkylene groups containing from 1 to 6 carbon atoms (especially —CH$_2$—, —(CH$_2$)$_2$— or —(CH$_2$)$_3$—); Y is —Si(R¹)$_3$ wherein each R¹ independently is unsubstituted alkyl (especially C$_{1-4}$-alkyl) or unsubstituted alkoxy (especially C$_{1-4}$-alkoxy), provided at least one R¹ is unsubstituted alkoxy; E is of formula (ii), (iii) or (iv) (especially of formula (ii)); and one group represented by R² is of formula —L¹—X wherein L¹ and X are as hereinbefore defined (with the preferences for E, L⁴, m, n and p as above) and the other group represented by R² is H, unsubstituted or substituted (as defined above) —CONH(C$_{1-20}$-alkyl), more especially H or —CONH (C$_{1-4}$-alkyl)).

An especially preferred compound of Formula (1) is that which has q=1, Y=Si(R¹)$_3$ and L²=(CH$_3$)$_2$ which reduces to the formula:

wherein, as before each R¹ independently is unsubstituted C$_{1-4}$-alkyl or unsubstituted C$_{1-4}$-alkoxy, provided at least one R¹ is unsubstituted C$_{1-4}$-alkoxy; and wherein further R² is H, —L¹X or —CONCH(C$_{1-4}$-alkyl) provided that one R² is H or —CONH(C$_{1-20}$-alkyl) and the other R² is —L¹X wherein X has L⁴=CH$_2$, m=1 and E of formula (ii) and L¹ is (CH$_2$)$_2$, which reduces —L¹X to the formula:

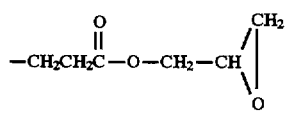

A second preferred class of epoxy compound is of Formula (2):

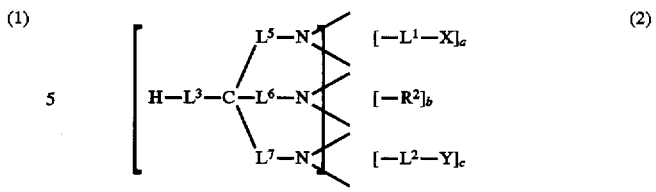 (2)

wherein:

L¹, L², X, and Y are as hereinbefore defined;
R² is H, unsubstituted or substituted alkyl where any substitution is as hereinbefore defined or —CO(C$_{1-4}$-alkylene)—CONH(C$_{1-4}$-alkyl), —CONH(C$_{1-6}$-alkyl) or —CO(C$_{1-4}$-alkylene—CO(C$_{1-4}$-alkyl);
L⁵, L⁶ and L⁷ are each independently divalent organic linker groups;
a is 2 to 6;
b is 6-(a+c);
c is 0 to 4; and
(a+b+c)=6.

An alternative class of epoxy compound having at least one epoxy group, at least one nitrogen atom and at least one hydrolysable silyl group is of Formula (2) wherein a is 1 to 5; b is 0 to 4; and c is 1 to 5; provided that (a+b+c)=6; each L¹, L², L⁵, L⁶, L⁷ and X are as hereinbefore defined and Y is of the formula —Si(R¹)$_3$ as hereinbefore defined.

E is preferably of formula (ii), (iii) or (iv) shown above.

The divalent organic linker groups L⁵, L⁶ and L⁷ are preferably optionally substituted alkylene, arylene or aralkylene. Preferred optionally substituted alkylene groups contain from 1 to 6 carbon atoms, more preferably 1 to 4 carbon atoms. A preferred optionally substituted arylene group is phenylene. A preferred optionally substituted aralkylene group contains from 7 to 10 carbon atoms, especially benzylene. The optional substituents which may be present on the divalent organic linker groups are preferably methyl, amino, ether, hydroxy or ester groups. The divalent organic linker groups may contain or be free from hetero linking atoms, for example ether or thioether groups.

Examples of preferred groups represented by L⁵, L⁶ and L⁷ include —CH$_2$—, —(CH$_2$)$_2$—, —(CH$_2$)$_4$—, —CH$_2$—CHOH—CH$_2$—, —CH$_2$—CH(OCOCH$_2$COCH$_3$)—CH$_2$—, —CH$_2$CH$_2$(OCH$_2$CH$_2$)$_{1or2}$—, —CH$_2$(OCH$_2$CH(CH$_3$))$_{1or2}$—, —C(CH$_2$CH$_3$)(X)—CH$_2$OCH(OH)—CH$_2$— (wherein X is as hereinbefore defined), —(CH$_2$)$_4$OCH(OH) CH$_2$— and phenylene.

When R² is H in Formula (2) the —NR²— group is a secondary amino group, and when R² is optionally substituted alkyl —NH²— is a tertiary amino group.

Components (a) and (b) are each independently dissolved or dispersed in the water. Thus the composition may be an aqueous dispersion or solution. "Aqueous dispersion" means a dispersion of a component in an aqueous carrier medium of which water is the principal component (usually at least 40 or 55 weight % of the carrier medium). Minor amounts of organic liquid(s) may be present if desired or required. Typically, component (b) will be in the form of an aqueous latex.

Compositions of the invention cross-link well to give film coatings having good mechanical properties and chemical resistance and some have low toxicity. The cross-linking may be performed at ambient temperatures without using toxic catalysts. If desired one may use a catalyst to speed up cross-linking still further. Suitable catalysts include secondary and tertiary amines, especially triethyl amine and tributylamine.

It is preferred that a substrate is coated using the composition of the present by applying the composition to a substrate, drying at ambient temperature and ageing the coating so formed at ambient temperature e.g. to develop cross-linking in the coating.

The invention also provides a process for forming a film or coating on a substrate comprising applying thereto a composition according to the invention and allowing water to evaporate therefrom, for example at a temperature of 10° C. to 30° C., or above 30° C. and below 250° C.

The weight ratio of component (a) to component (b) preferably lies in the range 0.1:100 to 35:100, more preferably 0.5:100 to 25:100, especially 1:100 to 15:100.

Carboxy functional polymer

The choice of carboxy functional polymer used as component (b) will depend upon the properties required for the cross-linkable composition. The carboxy functional polymer preferably has a number average molecular weight of from 100 or 500 to 500,000. Preferably the carboxy functional polymer contains an average of at least 1 carboxy group per molecule, more preferably at least 2. Polyesters, polyurethanes and olefinic polymers are preferred and may be used, provided they have a carboxy functionality.

As carboxy functional polymer there may be used an addition polymer or a condensation polymer, preferably formed by polymerisation of monomers which provide carboxy groups in the resultant polymer with monomers which do not provide carboxy or hydroxy groups in the resultant polymer.

The carboxy functional addition polymer is preferably formed by a free radical polymerisation process, more preferably under aqueous emulsion polymerisation conditions, preferably using a mixture of olefinically unsaturated carboxy functional monomers and olefinically unsaturated monomers which are free from hydroxy and carboxy groups. Alternatively, esters of the olefinically unsaturated monomers may be used to give an ester functional polymer and the ester groups hydrolysed to give the desired carboxy functional polymer.

The carboxy functional condensation polymer may be formed by condensation of a polyol and a polyacid (to give a polyester) or of a polyol and polyisocyanate (to give a polyurethane) or of a polyol, polyacid and polyisocyanate (to give a polymer having ester and urethane groups).

Preferred olefinically unsaturated carboxy functional monomers include olefinically unsaturated carboxylic acids, more preferably mono- and dicarboxylic acids, especially those having 3 to 5 or 6 carbon atoms, more especially acrylic acid, methacrylic acid, fumaric acid, itaconic acid and β-carboxyethyl acrylate (β-CEA).

Examples of olefinically unsaturated monomers which are free from carboxy and hydroxy groups include 1,3-butadiene, isoprene, styrene, divinyl benzene, acrylonitrile, methacrylonitrile, vinyl halides (e.g. vinyl chloride), vinylidene halides (e.g. vinylidene chloride), vinyl esters (e.g. vinyl acetate, vinyl propionate and vinyl laurate), (meth)acrylamides, heterocyclic vinyl compounds, alkyl esters of monolefinically unsaturated dicarboxylic acids (e.g. di-n-butyl maleate and di-n-butyl fumarate) and esters of acrylic acid and methacrylic acid of formula:

where $R^5$ is H or methyl and $R^1$ is an optionally substituted alkyl or cycloalkyl groups of 1 to 20 carbon atoms (more preferably 1 to 8 carbon atoms) or an alkoxysilane group, examples of which are methyl acrylate, methyl methacrylate, ethyl acrylate, ethyl methacrylate, n-butyl acrylate, n-butyl methacrylate, 2-ethylhexyl acrylate, 2-ethylhexyl methacrylate, isopropyl acrylate, isopropyl methacrylate, n-propyl acrylate, n-propyl methacrylate and various alkoxysilane functional acrylates and methacrylates; as mentioned supra $R^6$ may also be substituted and such substituents may e.g. be or include functional groups such as amino groups, olefinically unsaturated double bonds and halide atoms such as fluorine, and examples of such monomers include (t-butylamino) ethyl (meth) acrylate, allyl (meth) acrylate, 1,1,1-trifluoroethyl (meth) acrylate and hexafluoroisopropyl (meth) acrylate.

It is preferred that the carboxy functional addition polymer is derived from a mixture of monomers which comprise from 0.4 to 40% by weight of one or more carboxy functional monomers, more preferably 1.5 to 20%, by weight, and the remaining monomers which make the balance to 100% are free from carboxy and hydroxy groups.

Polymerisation of the monomers is normally effected in an aqueous medium and in particular aqueous emulsion polymerisation is used to prepare an aqueous latex of the polymer with conventional surfactants and initiators being used. The resulting latex of the polymer could be used "as is" in the composition (apart from optional dilution or concentration or the addition of coalescing solvent to assist in film formation) and can be partially or fully neutralised before use. Alternative radical polymerisation methods can be used, for example polymerisation in the bulk or in solution, followed by addition to water.

As mentioned above, polymers other than olefinic addition polymers can be used as the carboxy functional polymer. For example a polyurethane or polyester polymer bearing carboxyl groups (e.g. laterally or terminally disposed) can be used. As is well known polyurethane polymers (or analogous polymers such as polyurethane ureas or polyureas), are generally made by reacting an organic polyisocyanate with an organic compound containing at least two isocyanate-reactive groups, particularly a macropolyol with the optional inclusion of a low molecular weight polyol. A favoured route to their formation involves the formation of an isocyanate-terminated prepolymer followed by chain extension with an active hydrogen containing compound. A polyurethane bearing carboxy groups can be made by employing as a reactant, in the polyurethane prepolymer formation step, an isocyanate-reactive compound having at least one carboxy group and at least two isocyanate-reactive groups (such as 2,2-dimethylolpropionic acid), together with other compound (s) bearing isocyanate-reactive groups (usually polyol (s)), to form a prepolymer bearing lateral carboxy groups, followed by chain-extension with an active hydrogen containing compound (e.g. hydrazine or a diamino compound). Some of the carboxy groups of the polyurethane can be neutralised with an appropriate base to render it more readily water-dispersible, or the polyurethane could incorporate lateral or terminal or in-chain non-ionic groups (such as poly(oxyethylene) chain groups) to enhance water-dispersibility (or a combination of both expedients could be used).

Hydroxy functional polymers

Preferably the hydroxy functional polymer contains an average of at least 1 hydroxy group per molecule, more preferably at least 2.

Polyester polymers bearing hydroxy groups may be prepared by methods known in the art, for example by reacting an excess of a polyol with a diacid. Hydroxy functional polyurethane polymers may be prepared by methods known in the art, for example by reacting excess polyol with an isocyanate, or by reacting an isocyanate-terminated polyurethane with a hydroxyamine to give the desired hydroxy functionality.

Functional groups other than carboxy may be present in or absent from the hydroxy functional polymer, for example sulpho and/or phosphato groups may be present to aid water-solubility or dispersibility of the polymer. These groups may be incorporated using commercially available sulpho and phosphato functional monomers, for example sulphoethyl (meth)acrylate or acrylamidomethylpropanesulphonic acid.

Hydroxy functional polymers may be prepared by free radical polymerisation exactly as described above in relation to carboxy functional polymers except that an olefinically unsaturated hydroxy functional monomer is used in place of the olefinically unsaturated carboxy functional monomer.

Examples of olefinically unsaturated hydroxy functional monomers include N-methylol (meth)acrylamide, hydroxy $C_{2-8}$-alkyl esters of (meth)acrylic acid, e.g. hydroxyethyl (meth)acrylate, hydroxypropyl(meth)acrylate and mixtures thereof.

Polymers having carboxy and hydroxy functionality

Carboxy and hydroxy functionality may be introduced by a free radical polymerisation process, for example free radical polymerisation of a mixture comprising an olefinically unsaturated carboxy functional monomer (e.g. as described hereabove), an olefinically unsaturated monomer having at least one hydroxy group (e.g. as described hereabove), preferably in the presence of an olefinically unsaturated monomer which is free from carboxy and hydroxy groups. Examples of monomers which are free from carboxy and hydroxy groups are as hereinbefore described in relation to the carboxy functional polymer.

Two convenient routes for the preparation of hydroxy functional polyurethanes are described by P. B. Jacobs and P. C. Yu in J. Coatings Technology, 65, No. 822, July 1993. One route involves reacting an diol or polyol with a deficiency of isocyanate, for example a polyisocyanate is reacted with an excess of polyester diol and/or polyol and dimethylol propionic acid (DMPA) to produce a hydroxy terminated polyurethane oligomer having a carboxy group. A second route involves reacting a polyisocyanate, a polyol and DMPA to give an isocyanate terminated polymer which is reacted with an amino alcohol to give a hydroxy functional polyurethane polymer having a carboxy group.

Hybrid polymers having both hydroxy and carboxy functionality may also be used as component (b) of the composition. Such hybrids can be prepared by a number of methods including (a) polymerising a hydroxy functional monomer in the presence of a carboxy functional polymer, (b) polymerising a carboxy functional monomer in the presence of a hydroxy functional polymer, (c) polymerising a hydroxy functional monomer and/or a carboxy functional monomer in the presence of a polymer having both hydroxy and carboxy functionality, (d) polymerising a hydroxy functional monomer and a carboxy functional monomer in presence of a polymer having neither hydroxy or carboxy functionality, and (e) polymerising monomers which are free from hydroxy and carboxy groups in the presence of a polymer having both hydroxy and carboxy functionality.

The polymers referred to in (a), (b), (c), (d) and (e) above are preferably polyurethanes or polyesters. Usually the polymerisation method for forming hybrid polymers is free radical polymerisation process, and the hydroxy functional monomers and carboxy functional monomers are olefinically unsaturated hydroxy functional monomers and olefinically unsaturated carboxy functional monomers respectively, especially those described earlier in this specification.

In the case of free radical polymerisation of a hydroxy functional monomer or carboxy functional monomer in the presence of a polymer there is normally present one or more olefinically unsaturated monomers which are free from carboxy and hydroxy groups.

Mixtures comprising two or more of said Polymers

Mixtures and blends of polymers described for component (b) may also be used, for example a mixture comprising the aforementioned hydroxy functional polymer and carboxy functional polymer, or mixtures comprising either or both of these with the polymer having carboxy and hydroxy functionality.

The acid groups which may be present in components (a) and (b) may be in the free acid or salt form, preferably salt form.

The compositions of the invention preferably have a solids content within the range of from 10 to 70 wt. %, more preferably 30 to 50 wt. %.

The composition may be used as aqueous coating compositions to give films and coatings of excellent properties, and in particular excellent solvent resistance. For this purpose they may be used "as is" or further diluted with water and/or organic solvents, or they may be supplied in more concentrated form by evaporation of water and/or organic components of the liquid medium. As coating compositions, they may be applied to a variety of substrates including wood, paper, cardboard, metals, glass, cloth, leather, concrete, paper, plastics, foam and the like, by any conventional method including brushing, dipping, flow coating, spraying, and the like. The liquid carrier phase is removed (drying) at elevated or even at ambient temperatures, to form a film or coating. If desired the resultant film or coating can be heated at moderately elevated temperatures to accelerate the cross linking, although very often merely ageing the coating at ambient temperatures will be sufficient to develop excellent cross-linking.

The compositions may contain other conventional ingredients, including organic coalescing solvents, pigments, dyes, emulsifiers, surfactants, thickeners, heat stabilisers, levelling agents, wetting agents, anti-cratering agents, fillers, sedimentation inhibitors, fire retardants, UV absorbers, antioxidants and the like introduced at any stage of making the composition or subsequently.

The compositions may also be formulated as paints, adhesives or used as binders for printing inks or as overprint lacquers, varnishes and sealants.

The present invention also provides a film and a substrate coated by a film wherein the film is obtained or obtainable by evaporation of water from the composition according to the present invention. The preferred substrates are as described above.

The present invention is now illustrated by the following examples. Unless otherwise specified, all parts and percentages are by weight.

The MEK rub resistance test described in the examples assesses the solvent resistance of a film derived from a composition cast on a glass substrate and cured under the conditions indicated. A rag soaked in MEK is rubbed on the film to and fro until the film fails (i.e. is showing through) and the number of double rubs is recorded. If the film is still present at 200 double rubs it is rated as follows:

200 (0/5): film just failed 200 (1/5): film is severely affected 200 (2/5): film is affected 200 (3/5): film is slightly affected
200 (4/5): film is hardly affected
200 (5/5): film is unaffected The following abbreviations are used in the Examples:

AA=acrylic acid
BA=butylacrylate
HEA=hydroxyethylacrylate
MAA=methacrylic acid
MMA=methylmethacrylate
MEK=methylethylketone
β-CEA=beta-carboxyethylacrylate
APTMS=3-aminopropyltrimethoxysilane
APS=ammonium persulphate
Akyposal 9278R=sodium lauryl ether sulphate from Chem-y Chem. Fabrik GmbH, Germany.

EXAMPLE 1

Stage a)—Component (a)

Preparation of

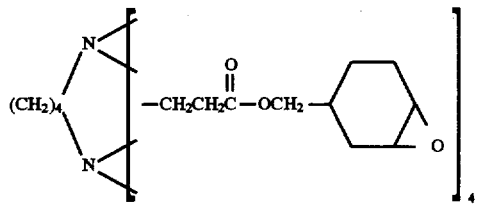

2,3-epoxycyclohexylmethylacrylate (36.4 g) was added to a stirred solution of 1,4-diaminobutane (4.4 g) in $CH_2Cl_2$ (40 cm$^3$) at 30° C. and the resultant mixture stirred at 20° C. for 4 days. Evaporation of the solvent gave the title product, having 4 alicyclic epoxy groups and two tertiary basic nitrogen atoms, as a yellow oil in approximately 98% yield.

Stage b)—Component (b)

A monomer emulsion was prepared by mixing deionised water (1275 g), Akyposal 9278R (250.2 g of a 30% solution in deionised water), APS (18.6 g), β-CEA (274.3 g), BA (1616.0 g) and MMA (1816.2 g). About 10% of the monomer emulsion was added to a vessel containing deionised water (2870 g) and Akyposal 9278R (83.4 g of a 30% solution in deionised water) of a 30% solution in deionised water and the mixture was stirred for 30 minutes, then heated to 85° C. and stirred for a further 30 minutes. The remaining monomer emulsion was added to the vessel over 2 hours whilst maintaining a temperature of 85°–88° C., then the temperature was raised to 90° C. and the mixture was stirred for 1 hour. The mixture was cooled to room temperature, filtered through a 200 µm screen and the filtrate was adjusted to pH6.8 using dilute aqueous ammonia.

The resultant carboxy functional polymer had the composition BA (43.6%), MMA (49.0%) and β-CEA (7.4%). The solids content was 43.5% w/w.

Stage c)—Composition

A composition was prepared by mixing equimolar parts of the product from component (a) with the product from stage b). (In this specification equimolar means the total number of carboxy groups in the polymer is equal to the number of epoxy groups in component (a)). The composition was found to be stable at 22° C. for several weeks. The composition was applied to glass at 22° C. using a Sheen Bar to give a wet film thickness of 100 µm. After heating at 52° C. for 18 hours, the resultant film was resistant to over 200 MEK double rubs (200⅗).

Stage d)—Comparative test

The method of stage c) was repeated and except that in place of the product from stage a) there was used 3,4-epoxycyclohexylmethyl-(3,4-epoxy)cyclohexane carboxylate which does not contain a nitrogen atom [ERC 4221]. The resultant film was found to be resistant to only 120 MEK double rubs.

EXAMPLE 2

Stage a)—Component (a)

Preparation of a polyepoxide of the formula $(R)_2NCH_2CH_2N(R)CH_2CH_2N(R)CH_2CH_2N(R)H_2$ wherein R is:

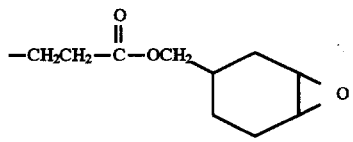

2,3-epoxycyclohexylmethylacryclate (91 g) was added over 1 hour to a solution of triethylene tetramine (12.2 g) in $CH_2Cl_2$(50 cm$^3$). Methanol (50 cm$^3$) was added to the mixture and, after 3 days, the solvents were evaporated to give the title product as a yellow/brown oil. $^1$H-NMR indicated approximately 95% yield of the title product having four tertiary basic nitrogen atoms and six alicyclic epoxy groups.

Stage b)—Component (b)

A carboxy functional polymer was prepared as described in Example 1, stage b).

Stage c)—Composition

A composition was prepared by mixing equimolar amounts of the product from stage a) with the product from stage b) based on the number of epoxide and carboxylic acid groups. The composition was found to be stable at 22° C. for several weeks. The composition was applied to glass and, after heating for 18 hours at 52° C., the resultant film was resistant to over 200 (200⅗) MEK double rubs showing it to be more effective than the film derived from 3,4-epoxycyclohexylmethyl -(3,4-epoxy)cyclohexane described in Example 1, stage c).

EXAMPLE 3

Stage a)—Component (a)

Preparation of a an epoxy compound of the formula $(R)_2N-CH(CH_3)CH_2(OCH_2CH(CH_3))_p-N(R)_2$ (from Jeffamine D230, available from Texaco) wherein R is as shown in Example 2 and p is about 3.

2,3-epoxycyclohexylmethylacryclate (91 g) was added to a solution of 30 g of an amine of formula $H_2NCH(CH_3)CH_2(OCH_2CH(CH_3))_p-NH_2$ equivalent wt active H of 60 in $CH_2Cl_2$ (50 cm$^3$). Methanol (50 cm$^3$) was added and the mixture left to stand until no double bonds were detected by $^1$H-nmr. The solvents were evaporated to give the above epoxy compound, having two basic nitrogen atoms and four alicyclic epoxy groups, as a pale yellow oil in approximately 95% yield.

Stage b)—Component (b)

A carboxy functional polymer was prepared as described in Example 1, stage b).

Stage c)—Composition

A composition was prepared by mixing equimolar amounts of the product from stage a) with the product from stage b). The composition was found to be stable at 22° C. for several weeks. The composition was applied to glass and, after curing at ambient temperature for 7 days or for 18 hours at 52° C., the resultant film was resistant to over 200 MEK double rubs. A control test in which the epoxy compound was absent gave an MEK double rub resistance of less than 20.

EXAMPLE 4

Stage a)—Component (a)

Preparation of an epoxy compound of the formula $(R)_2N$—$CH_2CH_2(OCH_2CH_2)_p$—$N(R)_2$ wherein p is about 2 and R is as shown in Example 2, having an equivalent wt based on active H of 36.

2,3-epoxycyclohexylmethylacryclate (91 g) was added to a solution of an amine of formula $H_2NCH_2CH_2$ $(OCH_2CH_2)_p$—$NH_2$ equivalent wt 36 (18 g, available as Jeffamine EDR 148 from Texaco) in $CH_2Cl_2$ (50 cm³). After standing for 10 days the solvent was evaporated to give the epoxy compound, having two basic nitrogen arc,ns and four alicyclic epoxy groups, as a yellow oil.

Stage b)—Component (b)

A carboxy functional polymer was prepared as described in Example 1, stage b).

Stage c)—Composition

A composition was prepared by mixing equimolar amounts of the product from stage a) with the product from stage b). The composition was found to be stable at 22° C. for several weeks. The composition was applied to glass plate and when heated at 52° C. for 18 hours, or left at ambient temperature for 7 days, gave a film which was resistant to over 200 MEK double rubs. A control test in which the epoxy compound was absent gave an MEK double rub resistance of less than 20.

EXAMPLE 5

Stage a)—Component (a)

Preparation of an epoxy compound of the formula

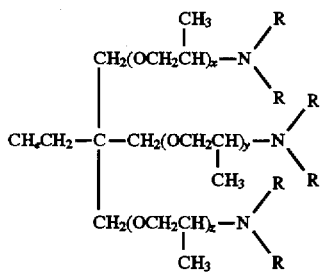

wherein x+y+z is from 5–6 and R is a defined in Example 2.

2,3-epoxycyclohexylmethylacrylate (91 g) was added to a solution of the above compound where R is H (40.5 g, NH equivalent=81, available as Jeffamine T403 from Texaco) in $CH_2Cl_2$ (60 cm³). Methanol (50 cm³) was added and, after standing for 25 days, the solvents were removed in vacuo to give the above compound having three tertiary basic N atoms and 5–6 epoxy groups in approximately 94% yield.

Stage b)—Component (b)

A carboxy functional polymer was prepared as described in Example 1, stage b).

Stage c)—Composition

A composition was prepared by mixing equimolar amounts of the product from stage a) with the product from stage b). The composition was found to be stable at 22° C. for several weeks. The composition was applied to a glass plate at 22° C. and after curing at room temperature for several days, or at 52° C. for 18 hours, a film formed which was resistant to over 200 MEK double rubs (200⅓). A control test in which the epoxy compound was absent gave an MEK double rub resistance of less than 20.

EXAMPLE 6

Stage a)—Component (a)

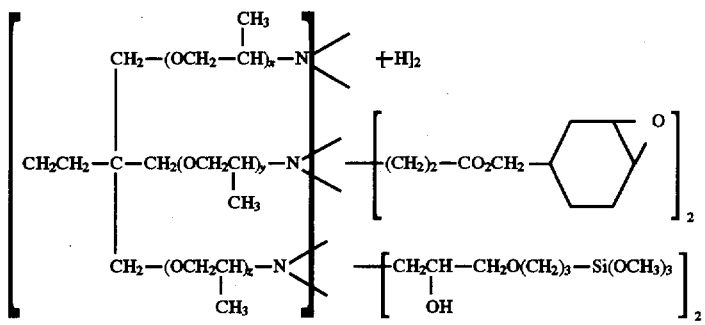

wherein x+y+z is from 5 to 6.

2,3-epoxycyclohexylmethylacrylate (0.2 moles) was added to a solution of Jeffamine T403 (40.5 g) CH$_2$Cl$_2$(35 cm$^3$) and methanol (25 cm$^3$). After 24 hours 0.2 moles of a compound of the formula:

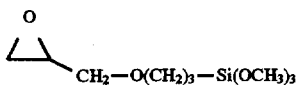

was added portionwise at 20° C. After 4 weeks standing the reaction was 95% complete and gave the title product, having three basic nitrogen atoms, two alicyclic epoxy groups and two hydrolysable silyl groups.

Stage b)—Component (b)

A carboxy functional polymer was prepared as described in Example 1, stage b).

Stage c)—Composition

A composition was prepared by mixing 6.8 parts of the product from stage a) with 100 parts of the product from stage b). The composition was found to be stable at 52° C. for several weeks. The composition was applied to glass and, when cured for 7 days at ambient temperature or 52° C. for 18 hours, the resultant film was resistant to over 200 MEK double rubs (200/s). A control test in which the epoxy compound was absent gave an MEK double rub resistance of less than 20.

Stage d)—Comparative test

The method of stage c) was repeated in an identical manner except that in place of the product from stage a) there was used ERC 4221 which does not have a basic nitrogen atom or a hydrolysable silyl group. The resultant film was resistant to less than 50 MEK double rubs.

EXAMPLE 7

Stage a)—Component (a)

Preparation of

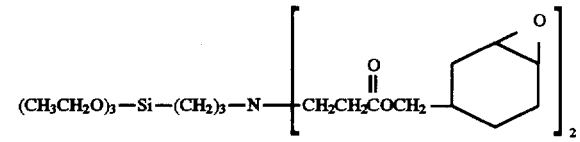

2,3-Epoxycyclohexylmethacrylate (36.4 g) was added to a stirred solution of 3-aminopropyltriethyoxysilane (22 g) in CH$_2$Cl$_2$ (50 ml). After 6 days stirring at room temperature the solvent was removed in vacuo to give the title product, which contains one basic nitrogen atom, two alicyclic epoxy groups and one hydrolysable silyl group, as a yellow oil.

Stage b)—Component (b)

A carboxy functional polymer was prepared by emulsion polymerisation of BA (43.6%), MMA (49%), β-CEA (7.4%) and was found to have 45% solids.

Stage c)—Composition

A composition was prepared by mixing 10 parts of the product from stage a), adjusted to pH 7.2, and an equimolar amount of the product from stage b). The composition was applied to glass and, after storage at room temperature for 7 days, the resultant film was resistant to over 200(4) MEK double rubs. A control test in which the epoxy compound was absent gave an MEK double rub resistance of less than 20.

EXAMPLE 8

Stage a)—Component (a)

Preparation of

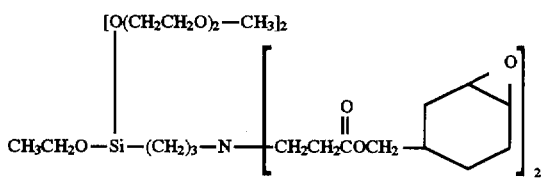

Methoxyethoxyethanol (0.4 moles) was added to 3-aminopropyltriethoxy silane (0.2 moles) and the mixture was heated at 130° C. for 3 hours. The mixture was cooled and $CH_2Cl_2$ (75 ml) added, followed by 2,3-epoxycyclohexylmethacrylate (0.4 moles). When no unsaturation was detected by $^1$H-NMR the solvent was removed in vacuo to give the title product, which contains one basic nitrogen atom, two alicyclic epoxy groups and one hydrolysable silyl group, as a yellow viscous oil.

Stage b)—Component (b)

A carboxy functional polymer was prepared as described in Example 7.

Stage c)—Composition

A composition was prepared by mixing 10 parts of the product from stage a) with an equimolar amount of the product from stage b). The composition was applied to glass and, after storage at room temperature for 7 days, the resultant film was resistant to 200% MEK double rubs. A control test in which the epoxy compound was absent gave an MEK double rub resistance of less than 20.

EXAMPLE 9

Stage (a) Preparation of epoxy compounds

Preparation I

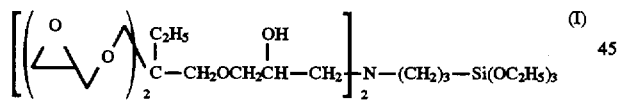

To trimethylolpropanetriglycidylether (4.5 g, "Heloxy 5048" ex Hi-Tek Polymers. Epoxide equivalent wt=145-165) was added 3-aminopropyl triethoxysilane (1.1 g); Epoxide:active NH 3:1. After 3 days at ambient temperature the ratio of epoxide groups to silicon was shown by NMR to be 2:1 corresponding to the above formula.

Preparation II

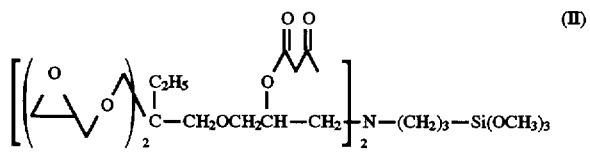

APTMS (11.1 g) was added to a solution of Heloxy 5048 (45 g) in dry $CH_2Cl_2$ (50 ml). After the exotherm had subsided the mixture was left at room temperature for 18 hours, then treated with freshly distilled diketene (8.4 g) and dimethylaminopyridine ("DMAP", 0.001 g). After a further 10 hours the solvent was evaporated to give the title product as a yellow oil.

Preparation III

The method for preparation of I was followed except that in place of the 4.5 g of Heloxy 5048 there was used 3.0 g. The resultant compound, named Preparation III, was less storage stable than Preparation I and gelled after a few days.

Preparation IV

To a 2 day old sample of preparation III (4.1 g) was added diketene (0.84 g) and a catalytic amount of DMAP. The product, namely Preparation IV, was found to be storage stable.

Preparation V

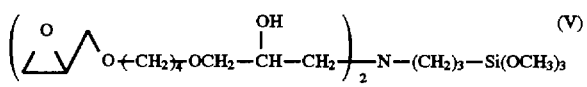

To butanedioldiglycidylether (20 g, 0.1M) was added APTMS (11.0 g, 0.05M) to give the title product having an initial epoxide to active NH ratio of 2:1. After 2 days at room temperature the product was found relatively unchanged. After 6 days the product had gelled.

Preparation VI

Preparation V was treated with diketene in an analogous manner to that described in Preparation II above. The resultant product, namely Preparation VI, was found to be storage stable.

Preparation VII

To APTMS (35.8 g, 0.2M) was added vinylcyclohexene-dioxide (28 g, 0.2M). The mixture was warmed to 50° C. for 18 hours after which all the primary amine had reacted. The product gelled after 2 months.

Preparation VIII—Comparative Example

Butanedioldiglycidylether (20 g, 0.1M) and aminopropyltriethoxysilane (11.0 g, 0.05M) were added individually (i.e. without reacting them together) to the carboxy functional polymer described below under Test Results.

Stage (b)—preparation of Polymer

A carboxy functional polymer was prepared exactly as described in Example 1, stage (b), except that in place of β-CEA there was used AA (136.6 g) and the amount of BA was increased to 1753 g. The resultant polymer had the composition BA (47.3%), MMA (49%) and AA (3.7%) and a solids content of 45%.

Stage (c)—Test Results of Preparations I to VIII

The carboxy functional polymer described in stage (b) above was added to the weight of the product I-VIII shown in Table I below. The resultant compositions were cast as films onto glass plates using a 100 μm Sheen Bar and evaluated according to the cure schedules shown by rubbing the films with cotton wool soaked in MEK.

TABLE 1

|  |  | CURE/MEK RUB RESISTANCES | | |
|---|---|---|---|---|
| Pre-paration | Wt % Preparation to polymer | After 52° C./2hrs | After room-temperature/ 2 days | After room-temperature/ 7 days |
| — | CONTROL | 10 | 10 | 10 |
| I | 5.6 | 60 | 200 (0) | 200 (3) |
| II | 6.4 | 60 | 120 | 200 (1) |
| III | 8.2 | 90 | 180 | 200 (3) |
| IV | 16.0 | 80 | 150 | 200 (2) |
| V | 6.2 | 200 (0) | 190 | 200 (3) |
| VI | 7.9 | 180 | 180 | 200 (3) |
| VII | 6.4 | 200 (3) | 170 | 200 (3) |
| VIII | 5.1 (a) 1.2 (b) | 20 | 25 | 30 |

Note:
(a) = Butanediolglycidyl ether
(b) = Aminopropyltriethoxysilane
In VIII unreacted ingredients (a) and (b) were added to the polymer.

In VIII unreacted ingredients (a) and (b) were added to the polymer.

EXAMPLE 10

Preparation of further epoxy compounds by Michael Addition Reactions

Preparation IX

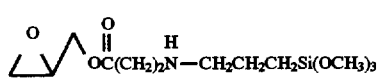
(IX)

APTMS (17.9 g) was added dropwise, with stirring over 15 minutes, to ice-cooled glycidylacrylate (12.9 g). After 2 hours, NMR indicated that the title preparation IX had been formed. Preparation IX was found to be stable for a few hours.

Preparation X

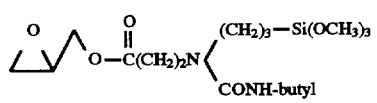
(X)

Butylisocyanate (9.9 g) was added to a cold fresh solution of Preparation IX. After 2 hours title Preparation X had been formed and was found to be storage stable.

Preparation XI

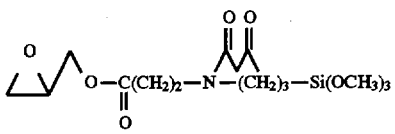
(XI)

Preparation IX (30.8 g) was treated dropwise with diketene (8.4 g) to give the title Preparation XI.

Preparation XII

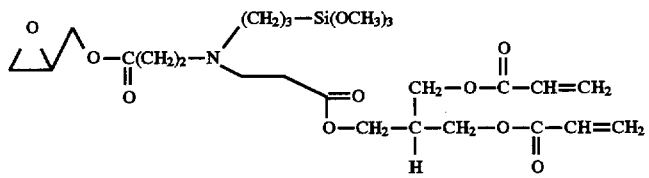
(IX)

To a fresh sample of Preparation IX was added 1 equivalent of TMPTA (Trimethylolpropanetriacrylate) (a three fold excess of acrylic groups to —NH— group) to give the title product as a storage stable liquid.

Preparation XIII (XIII)

$$\left( \bigtriangleup\!\!\!\!\!\!\!\!\!\!\!\!\!\diagdown\!\!\!\!\!\!\diagup O-\underset{\underset{O}{\|}}{C}(CH_2)_2 \right)_2 \!\!\!\!\!- N-(CH_2)_3-Si(OCH_3)_3$$

APTMS (8.84 g, 0.045M) was added a solution of glycidyl acrylate (13 g, 0.1M) in dry $CH_2Cl_2$ (15 ml). The temperature rose to 33° C. and the mixture was stood for 3 days, after which unsaturation had reduced to a steady value equivalent to 80% conversion of starting materials to title preparation. A further portion of APTMS (2 g) was added. After 1 month the product had gelled.

Preparation XIIIA

Preparation XIII was reacted with butylisocyanate to give Preparation XIIIA.

Preparation XIIIB

Preparation XIII was reacted with diketene to give Preparation XIIIB.

Preparation XIV

Isophorone diisocyanate (11.0 g) was added dropwise with stirring to a solution of Preparation IX (30.8 g) in dry $CH_2Cl_2$ (50 ml) at 0°–5° C. After standing for 16 hours the $CH_2Cl_2$ was removed in vacuo to give preparation XIV as a clear viscous oil.

Preparation XV $$XL^1-N(R^2)-CH_2CH_2-N(R^2)-(CH_2)_3-Si(OCH_3)_3 \quad (XV)$$

wherein one $R^2$ is H and the other $R^2$ is —$L^1X$ where —$L^1X$ has the formula:

$$-CH_2CH_2\overset{O}{\overset{\|}{C}}-O-CH_2-\underset{O}{\triangle}$$

$H_2NCH_2CH_2NH(CH_2)_3$—$Si(OCH_3)_3$ (22.2 g) in dry $CH_2Cl_2$ (50 ml) was added over ½ hour, with stirring, to a solution of glycidyl acrylate (25.6 g) in dry $CH_2Cl_2$ (50 ml) at 0° C. After 5½ hours NMR indicated the formation of Preparation XV having very low residual unsaturation.

Preparation XVA

Preparation XV (23.9 g) was reacted with butylisocyanate (5 g) to give preparation XVA, having the formula XV shown above but with a —CO—NH—Butyl group in place of the hydrogen atom represented by $R^2$.

Preparation XVB

Preparation XV (23.9 g) was reacted with diketene (4.3 g) to give preparation XVB, having the formula XV shown above but with a —$COCH_2COCH_3$ group in place of the hydrogen atom represented by $R^2$.

Preparation XVI $$\text{(cyclohexene oxide)}-CH_2OC(=O)-CH_2CH_2-N(H)-(CH_2)_3-Si(OCH_3)_3 \quad (XVI)$$

2,3-Epoxycyclohexylmethylacrylate (125 g, "Cyclomer A200", available from Diacel) was added over 30 minutes to APTMS (123 g). After 1 day stirring the title preparation XVI was isolated and found to be storage stable.

Preparation XVII

Preparation XVI was reacted with one equivalent of diketene at 20°–25° C. to give preparation XVII.

Preparation XVIIA

Preparation XVI was reacted with one equivalent of butylisocyanate to 20°–25° C. to give preparation XVIIA.

Preparation XVIII $$\left(\text{(cyclohexene oxide)}-CH_2-O-\underset{O}{\overset{\|}{C}}-N(CH_2)_3-Si(OCH_3)_3\right)_2 \quad (XVIII)$$

APTMS (17.9 g, 0.1M) was added to a solution of Cyclomer A200 (36.4 g, 0.2M) in $CH_2Cl_2$ (50 ml) and methanol (10 ml). After 3 days NMR indicated that the reaction was complete giving preparation XVIII as a storage stable material.

Preparation XIX $$R-NCH_2CH_2N(R)(CH_2)_3Si(OCH_3)_3 \quad (XIX)$$

wherein one R is H and two groups represented by R are as defined in Example 2.

Cyclomer A200 (0.1M) was added dropwise with stirring to $H_2NCH_2CH_2NH(CH_2)_3Si(OCH_3)_3$(0.2). After standing at room temperature for 1½ days NMR indicated that the title preparation XIX had been formed. Preparation XIX was found to be storage stable.

Preparation XX

Preparation XX was made according to the method described in Example 6, stage a).

Preparation XXI

The method described above for Preparation XV was followed except that in place of glycidyl acrylate there was used 2,3-epoxycyclohexylmethylacrylate. The product, namely Preparation XXI, was obtained as a storage-stable pale yellow liquid.

Test Results of Preparations IX to XXI

The carboxy functional polymer described in Example 9, stage (b) was treated individually with Preparations IX to XXI before casting onto glass plates using a 100 μm Sheen Bar and evaluating MEK rub resistance. The results are shown in Table 2:

TABLE 2

| | | CURE/MEK RUB RESISTANCE | | | | |
|---|---|---|---|---|---|---|
| Preparation | Wt % of Preparation to polymer | After 1 day | After 2 days | After 4 days | After heating at 52° C. 3 hrs | After heating at 52° C. for 18 hrs |
| IX | 6.1 | 200 (3) | — | 200 (4) | 200 (4) | — |
| X | 8.0 | 40 | 200 (0) | 200 (3) | — | 200 (2) |
| XI | 8.0 | 80 | — | 200 (3) | — | 200 (0) |
| XII | 9.1 | 200 (2) | — | 200 (4) | — | 200 (4) |
| XIII | 4.0 | 200 (2) | 200 (4) | — | 200 (3) | — |
| XIIIA | 4.8 | 200 (1) | 200 (3) | 200 (4) | 200 (3) | — |
| XIIIB | 4.9 | 200 (2) | 200 (3) | — | 200 (4) | — |
| XIV | 8.4 | 100 | 120 | — | — | 100 |
| XV | 5.0 | 200 (3) | 200 (4) | — | 200 (3) | 200 (4) |
| XVA | 5.1 | 200 (2) | 200 (3) | — | 200 (3) | 200 (4) |
| XVB | 5.3 | 200 (2) | 200 (4) | — | 200 (3) | 200 (4) |
| XVI | 7.2 | 90 | 200 (1) | — | 100 | — |
| XVII | 8.9 | 20 | 30 | — | 20 | — |
| XVIII | 5.4 | 50 | 200 (0) | 200 (3) | 200 (2) | — |
| XIX | 5.8 | — | — | 200 (2) | 200 (2) | 200 (4) |
| XX | 6.8 | — | — | 200 (2) | — | 200 (4) |
| XXI | 12.9 | — | — | 220 (2) | — | 200 (4) |
| Control | — | <20 | <20 | <20 | <20 | <20 |

EXAMPLE 11

Preparation XXII

The method described in Example 10, Preparation XV, was followed except that in place of $H_2NCH_2CH_2NH(CH_2)_3$—$Si(OCH_3)_3$ there was used $H_2NCH_2CH_2NH(CH_2)_3$—$SiCH_3$ $(OCH_3)_2$, to give Preparation XXII.

Preparation XXIII

Methyl polyethylene glycol methacrylate (0.04M, 25.4 g, available from B. P. Chemicals as MPEG 550 MA) was added to $H_2NCH_2CH_2NH(CH_2)_3Si(OCH_2)_3$ (0.2M, 44.4 g) and the mixture stood for 2 days at 52° C. Glycidyl acrylate (0.34M, 43.5 g) was added at room temperature over 30 minutes. The temperature rose to 30° C. and the mixture was maintained at 30° C. for 6 hours, cooled to 10° C. and treated with butyl isocyanate (2.0M, 19.8 g). The resultant product was found to be dispersible in water.

EXAMPLE 12

Preparation and Comparison of Carboxy Polymers with Polymers having Carboxy and Hydroxy Functionality Step a)—A polymer having carboxy and hydroxy functionality was prepared as follows (hereinafter the "OH+COOH polymer").

A 1 liter round bottom flask was fitted with a stirrer, dropping funnel and thermometer was purged with nitrogen gas. A solution of Alkyposal 9278R surfactant (7.4 g) in water (280 ml) was added to the flask. An emulsion comprising water (112 g), MAA (14.6 g), HEA (19.6 g), MMA (138 g), BA (155 g), Alkyposal 9278R (22 g) and ammoniumpersulphate (1.64 g) was charged into the dropping funnel. Approximately 10% of the dropping funnel contents was added to the flask and the flask was then heated to 85° C. The remaining contents of the dropping funnel were added dropwise over 1.5 hours and the flask was heated at 85° C. for a further 1 hour. The flask contents were filtered and the filtrate cooled to give the OH+COOH polymer as a low viscosity white emulsion having a solids content of about 44%.

Step b)—Preparation of a polymer having carboxy groups and no hydroxy groups (hereinafter the "carboxy polymer").

A carboxy polymer was prepared exactly as described in Example 1, stage (b), except that in place of β-CEA there was used MAA (165 g), the amount of BA was increased to 1812 g and the amount of MMA was decreased to 1726 g. The resultant polymer contained MAA (4.45%), MMA (46.6%) and BA (48.9%).

Step c)—Evaluation

The polymers described in steps a) and b) were adjusted to pH 6.8 and treated with the cross-linker preparations mentioned in the first column of Table 3. The second column states the amount of preparation used (weight % relative to the polymer).

TABLE 3

| Preparation | Wt % of Preparation to polymer | Polymer | CURE/MEK RUB RESISTANCE | | |
|---|---|---|---|---|---|
| | | | 1 day RT | 2 days RT | 5 days RT |
| XVA | 7.2 | OH + COOH | 200 (3) | 200 (5) | — |
| XIIIA | 4.0 | OH + COOH | 200 (4) | 200 (5) | — |
| XIIIA | 4.0 | Carboxy | 100–200 | 200 (2) | — |
| XVIII | 5.4 | OH + COOH | 40–50 | 200 (0) | 200 (4) |
| XVIII | 5.4 | Carboxy | <20 | 30–40 | 50–60 |
| XXI | 5.0 | OH + COOH | 90 | — | 200 (4) |
| XXI | 5.0 | Carboxy | 20–30 | — | 40–50 |
| None | — | OH – $CO_2$ | <20 | <20 | <20 |
| None | — | Carboxy | <20 | <20 | <20 |

Table 3 shows that compositions comprising the crosslinker preparations and a polymer having both carboxy and hydroxy functionality have higher MEK rub resistance than compositions where the polymer has only carboxy groups.

We claim:

1. A compound of Formula (1):

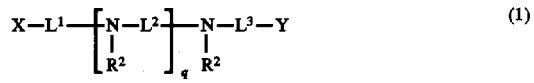

wherein:

X is $E—(L^4O)_m—CO—(T)_p$;

Y is $—Si(R^1)_3$ or X as defined above;

T is O, $CH_2$ or $NR^2$;

P is 0 or 1;

q is 0, 1, 2, 3 or 4;

E comprises an alicyclic or aliphatic epoxy group;

each $L^1$, $L^2$, $L^3$ and $L^4$ independently is an unsubstituted or substituted alkylene group of 1 to 6 carbon atoms wherein any substitution is selected from methyl, amino, ester, hydroxy and ester groups;

m is 0 or 1;

each $R^1$ when Y is $—Si(R^1)_3$ is independently unsubstituted alkyl or substituted alkoxy provided that at least one $R^1$ is unsubstituted alkoxy; and each $R^2$ independently is H, $—L^1X$ or unsubstituted or substituted alkyl wherein any substitution is selected from the group consisting of poly(oxyalkylene), epoxy and hydrolyzable silyl groups, or $—CONH(C_{1-20}$-alkyl).

2. A compound according to claim 1 wherein $L^1$, $L^2$, $L^3$ and $L^4$ are each independently $—CH_2—$, $—(CH_2)_2—$ or $—(CH_2)_3—$;

each $R^1$ independently is $C_{1-4}$-alkoxy or $C_{1-4}$-alkyl, provided at least one $R^1$ is $C_{1-4}$-alkoxy; and one $R^2$ is H or $—CONH(C_{1-20}$-alkyl) and any other $R^2$ is $—L^1X$ where m=1 and p=0 in X whereby such other $R^2$ has the formula $—L^1—CO—O—L^4—E$ with $L^1$, $L^4$ and E as defined in claim 1.

3. A compound according to claim 1 in which q=1, $Y=Si(R^1)_3$ and $L^2$ is $(CH_2)_2$ which reduces to the formula:

wherein each $R^1$ independently is $C_{1-4}$-alkyl or $C_{1-4}$-alkoxy, provided at least one $R^1$ is $C_{1-4}$-alkoxy; and wherein further $R^2$ is H, $—L^1X$ or $—CONH(C_{1-20}$-alkyl) provided that one $R^2$ is H or $—CONH(C_{1-20}$-alkyl) and the other $R^2$ is $—L^1X$ where X has $L^4=CH_2$, m=1 and E of formula (ii) and $L^3$ is $(CH_2)_2$ which reduces $—L^1X$ to the formula:

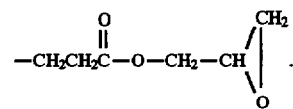

4. A compound according to claim 1 wherein m=q=1; p=0; Y is $—Si(R^1)$ wherein each $R^1$ as defined in claim 1; E is of formula (ii), (iii) or (iv)

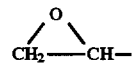 (ii)

-continued

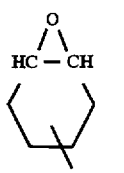

(iii)

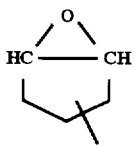

(iv)

and one group represented by $R^2$ is of formula —$L^1$—X wherein $L^1$ and X are defined in claim 1 and the other group represented by $R^2$ is H, unsubstituted alkyl or —CONH ($C_{1-20}$-alkyl).

5. A compound according to claim 1 of the formula

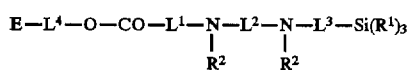

wherein

E is of the formula (ii), (iii) or (iv):

$$H_2C\underset{O}{\diagdown}CH—$$ (ii)

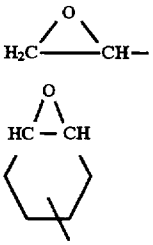

(iii)

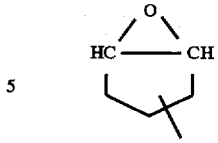

(iv)

$L^1$, $L^2$, $L^3$ and $L^4$ are each independently —$CH_2$—, —$(CH_2)_2$— or —$(CH_2)_3$—; each $R^1$ is as defined in claim 1 and one $R^2$ is —$L^1$X wherein m=1 and p=0 in X, which reduces —$L^1$X to the formula —$L^1$—CO—O—$L^4$—E, and the other $R^2$ is H or —CONH($C_{1-20}$-alkyl).

6. A compound according to claim 1 in which q=1, Y=Si(OCH$_3$)$_3$, $L^2$=(CH$_2$)$_2$ and $L^3$=(CH$_2$)$_3$, which reduces to the formula

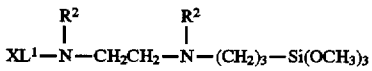

and wherein further one $R^2$ is —CO—NH—butyl and the other $R^2$ is $L^1$X where X has $L^4$=CH$_2$, m=1 and E of formula (ii) which reduces —$L^1$X to the formula:

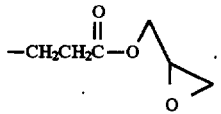

* * * * *

UNITED STATES PATENT AND TRADEMARK OFFICE
CERTIFICATE OF CORRECTION

PATENT NO. : 5,674,965
DATED : October 7, 1997
INVENTOR(S) : John Gerard CAREY
Christopher PADGET
David Alan PEARS It is certified that error appears in the above-identified patent and that said Letters Patent is hereby corrected as shown below:

Column 3, line 28, change "invention preferably" to --invention. Preferably--;

Column 3, line 42, change "-CONH($C_{1-20}$ - alkyl)" to ---alkyl, or CONH($C_{1-20}$ - alkyl)---;

Column 3, line 55, change "-CONCH($C_{1-4}$ - alkyl)" to ----CONH($C_{1-20}$ - alkyl)---;

Column 12, line 16, change left most group in the formula to ---$CH_3CH_2$---;

Column 22, line 33, change "-$(CH_2)^2$ -" to --- -$(CH_2)_2$- ---; and

Column 22, line 61, change "Si($R^1$)" to ---Si($R^1$)$_3$---.

Signed and Sealed this

Seventeenth Day of March, 1998

Attest:

BRUCE LEHMAN

Attesting Officer

Commissioner of Patents and Trademarks